United States Patent [19]
Melzer

[11] Patent Number: 5,582,699
[45] Date of Patent: Dec. 10, 1996

[54] PH GLASS ELECTRODE

[75] Inventor: Werner Melzer, Liederbach, Germany

[73] Assignee: Hoechst Aktiengesellschaft, Germany

[21] Appl. No.: 460,432

[22] Filed: Jun. 2, 1995

Related U.S. Application Data

[62] Division of Ser. No. 190,599, Feb. 2, 1994, abandoned.

[30] Foreign Application Priority Data

Feb. 4, 1993 [DE] Germany ............ 43 03 186.2

[51] Int. Cl.⁶ .................................................. G01N 27/36
[52] U.S. Cl. ..................... 204/420; 204/435; 205/787.5
[58] Field of Search ................................. 204/420, 435; 205/787.5

[56] References Cited

U.S. PATENT DOCUMENTS

| | | | |
|---|---|---|---|
| 2,677,655 | 5/1954 | Klumb | 204/197 |
| 3,652,439 | 3/1972 | Ben-Yaakov et al. | 204/420 |
| 4,569,224 | 2/1986 | Fukumoto et al. | 204/409 |

FOREIGN PATENT DOCUMENTS

| | | | |
|---|---|---|---|
| 492936 | 9/1938 | United Kingdom | 204/420 |
| 667471 | 3/1952 | United Kingdom | 204/420 |

OTHER PUBLICATIONS

International Electrotechnical Commission, IEC Standard, "Expression of Performance of Electrochemical Analyzers", Part 2: pH value, Publication 746–2, First Ed., 1982.

*Primary Examiner*—T. Tung
*Attorney, Agent, or Firm*—Curtis, Morris & Safford, PC

[57] ABSTRACT

In the pH glass electrode comprising a double-walled glass tube in which an electrical screen is provided between the walls, the inner glass tube is sealed at one end with a glass lid and at the other end with a pH-sensitive glass membrane which forms, with the glass tube, a cavity which is filled with internal reference solution and into which the reference electrode extends. A feed tube (10) and a drain tube (11) which are passed through the lid (5) and intended for the internal reference solution (8) are disposed in the internal glass tube (3), the drain tube (11) extending down to the lowest point in the cavity (7).

18 Claims, 1 Drawing Sheet

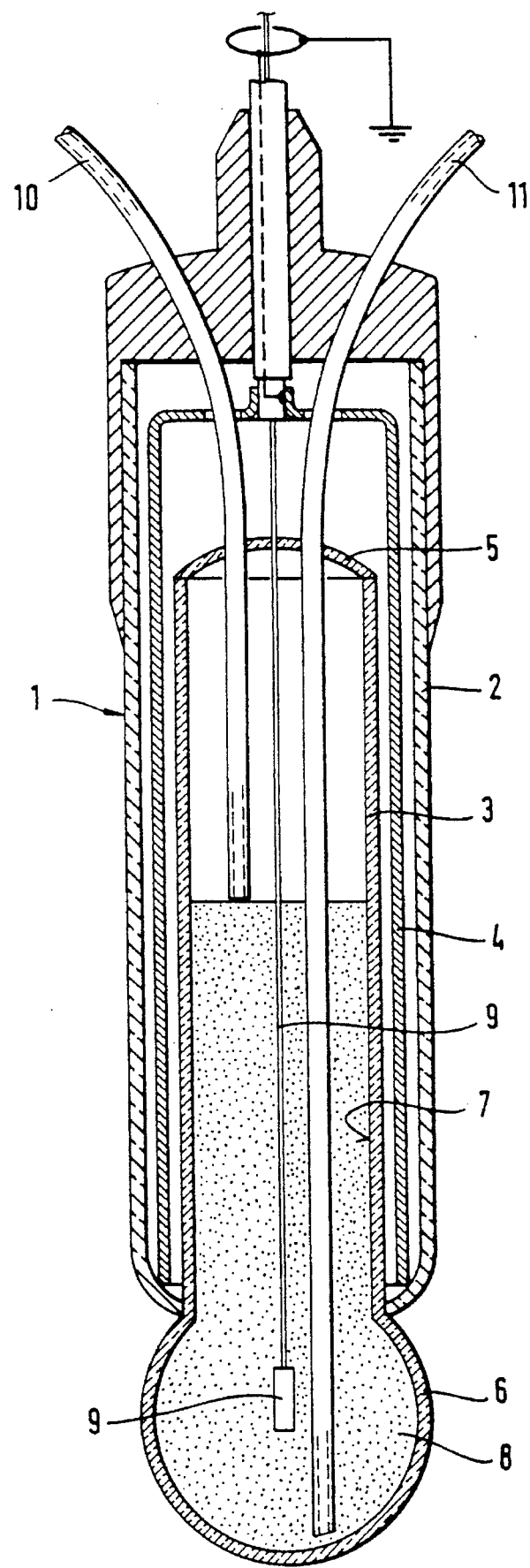

PH GLASS ELECTRODE

This application is a division of application Ser. No. 08/190,599, filed Feb. 2, 1994, now abandoned.

The invention relates to a pH glass electrode which comprises a double-walled glass tube in which an electrical screen is provided between the walls of the outer glass tube and inner glass tube and the inner glass tube is sealed at one end with a glass lid and at the other end with a pH-sensitive glass membrane which forms, with the glass tube, a cavity which is filled with internal reference solution and into which the reference electrode extends.

Whereas the measuring-cell zero point of modern pH measuring cells remains largely stable, the measuring-cell slope has to be calibrated at certain intervals of time. For this purpose, the measuring cells are removed from the container, the continuous-flow vessel or the pipe and calibrated externally in known buffers. During this process, the measuring-cell data, such as measuring-cell zero point and measuring-cell slope, are determined and their deviations compensated for on the pH meter. The calibration operation can often not be carried out at processing temperatures but only at room temperature. The time required is 1 to 2 hours. For this reason, and also because of the costs associated therewith, a frequent calibration, for example to increase the measuring accuracy, has generally to be dispensed with.

It is furthermore known to withdraw the measuring cells pneumatically from the test solution and expose them to rinsing solutions and calibrating solutions. The deviations in the measuring-cell parameters found in this process are compensated for in the pH meter. Such systems are relatively complex and expensive. Problems are presented, in particular, by the wear associated with the pneumatic movement of the measuring cell and the satisfactory sealing of the test liquid, ie. its retention in the container.

The invention avoids these difficulties. The measuring cell always remains in the fixed position of the measuring point.

The invention achieves the object as a result of the fact that a feed tube and a drain tube which are passed through the lid and intended for the internal reference solution are provided in the inner glass tube, the drain tube extending down to the lowest point in the cavity.

The advantages achieved with the invention are to be seen essentially in the fact that the measuring-cell slope, the most important parameter, can be calibrated by simply replacing the internal reference solution inside the glass electrode without removing the pH glass-electrode measuring cell. The measuring-cell slope is the quotient of the difference in the measured potentials on replacing the reference solution and the difference in the known pH values of the replaced internal reference solution 8. The calibration is carried out at the product temperature prevailing at the time. The expenditure on control or evaluation of the calibration operation is small.

BRIEF DESCRIPTION OF THE DRAWINGS

FIG. 1 shows a longitudinal section through the pH glass electrode of the present invention.

The invention is explained in greater detail below with reference to the figure showing an exemplary embodiment.

The pH glass electrode comprises a double-walled glass tube 1. An electrical screen 4 is provided between the walls of the outer glass tube 2 and of the inner glass tube 3. The inner glass tube 3 is sealed at one end with a glass lid 5 and at the other end with a pH-sensitive glass membrane 6, which may be spherical. The glass membrane 6 forms, with the inner tube 3, a cavity 7 which is filled with internal reference solution 8 and into which the reference electrode 9 extends. A feed tube 10 and a drain tube 11 which are passed through the lid 5 and are intended for the internal reference solution 8 are disposed in the inner glass tube 3, the drain tube 11 extending to the lowest point in the cavity 7.

I claim:

1. A method for calibrating measuring-cell slope of a pH glass electrode without having to remove the pH glass electrode from measuring point position, said pH glass electrode having a sealed glass tube sealed at an end with a pH-sensitive glass membrane, means defining a cavity within the tube, the cavity having a low point towards the end of the tube sealed with the pH-sensitive membrane, and, an internal reference solution in the internal cavity into which an internal reference electrode extends, said method comprising:

provising said pH glass electrode with a feed tube and a drain tube extending into the cavity, wherein the drain tube extends proximate to the low point of the cavity, determining a first difference in measured potential from a known pH value of the internal reference solution, replacing the solution by means of the drain tube and feed tube with fresh internal reference solution, determining a second difference in measured potential from a known pH value of the fresh internal reference solution, and determining a quotient of the second difference and the first difference.

2. The method of claim 1 wherein the pH-sensitive glass membrane is spherical in shape.

3. The method according to claim 1, wherein the drain tube extends down vertically to the low point of the cavity.

4. The method according to claim 1, wherein the feed tube and the drain tube are substantially parallel.

5. A method for calibrating measuring-cell slope of a pH glass electrode without having to remove the pH glass electrode from measuring point position, said method comprising:

providing a pH glass electrode at a measuring point position, determining a first difference in measured potential from a known pH value of an internal reference solution, replacing the internal reference solution with a fresh internal reference solution without removing the pH glass electrode from the measuring point position, determining a second difference in measured potential from a known pH value of the fresh internal reference solution, and, determining a quotient of the second difference and the first difference.

6. The method of claim 5, wherein the pH glass electrode comprises:

an inner glass tube having:
a first end sealed with a glass lid,
a second end sealed with a pH-sensitive glass membrane,
means defining a cavity within the inner glass tube, said cavity having a low point towards the second end of the inner glass tube, and
an exterior surface, the internal reference solution within the cavity, an outer glass tube disposed over the inner glass tube, said outer glass tube having:

an interior, an end contacting the exterior surface of the inner glass tube and beyond which the second end of the inner glass tube extends, an electrical screen disposed within the interior of the outer glass tube and over the exterior surface of the inner glass tube, a reference electrode passing through the outer glass tube, the electrical screen and the glass lid and extending into the reference solution, and a feed tube and a drain tube, each passing through the electrical screen and the glass lid and extending into the cavity, wherein the drain tube extends proximate to the low point of the cavity.

7. The method of claim 6 wherein the pH-sensitive glass membrane is spherical in shape.

8. The method according to claim 6, wherein the drain tube extends down vertically to the low point of the cavity.

9. The method according to claim 6, wherein the feed tube and the drain tube are substantially parallel.

10. A method for replacing internal reference solution in a pH glass electrode without having to remove the pH glass electrode from measuring point position, said pH glass electrode having a sealed glass tube sealed at an end with a pH-sensitive glass membrane, means defining a cavity within the tube, the cavity having a low point towards the end of the tube sealed with the pH-sensitive membrane, a solution in the internal cavity, and, an internal reference electrode extending into the solution, said method comprising:

providing said pH glass electrode with a feed tube and a drain tube extending into the cavity, wherein the drain tube extends proximate to the low point of the cavity, and draining solution from the cavity via the drain tube and, feeding solution to the cavity via the feed tube.

11. The method of claim 10, wherein the pH-sensitive glass membrane is spherical in shape.

12. The method according to claim 10, wherein the drain tube extends down vertically to the low point of the cavity.

13. A method for replacing internal reference solution in a pH glass electrode without having to remove the pH glass electrode from measuring point position, said method comprising:

providing a pH glass electrode, draining used internal reference solution from a cavity via a drain tube and, feeding fresh internal reference solution to the cavity via a feed tube, wherein the pH glass electrode comprises:

an inner glass tube having:

a first end sealed with a glass lid, a second end sealed with a pH-sensitive glass membrane, means defining a cavity within the inner glass tube, said cavity having a low point towards the second end of the inner glass tube, and an exterior surface, an internal reference solution within the cavity, an outer glass tube disposed over the inner glass tube, said outer glass tube having:

an interior, an end contacting the exterior surface of the inner glass tube and beyond which the second end of the inner glass tube extends, an electrical screen disposed within the interior of the outer glass tube and over the exterior surface of the inner glass tube, a reference electrode passing through the outer glass tube, the electrical screen and the glass lid and extending into the reference solution, and the feed tube and the drain tube, each passing through the electrical screen and the glass lid and extending into the cavity, wherein the drain tube extends proximate to the low point of the cavity.

14. The method of claim 13 wherein the pH-sensitive glass membrane is spherical in shape.

15. A method for calibrating measuring-cell slope of a pH glass electrode without having to remove the pH glass electrode from measuring point position, said method comprising:

providing a pH glass electrode, determining a first difference in measured potential from a known pH value of an internal reference solution, replacing the internal solution by means of a drain tube and feed tube with fresh internal reference solution, determining a second difference in measured potential from a known pH value of the fresh solution, and, determining a quotient of the second difference and the first difference, wherein the pH glass electrode has a sealed glass tube sealed at an end with a pH-sensitive glass membrane, means defining a cavity within the tube, the cavity having a low point towards the end of the tube sealed with the pH-sensitive membrane, and, the internal reference solution in the internal cavity, and, an internal reference electrode extending into the solution, said pH glass electrode characterized by the feed tube and the drain tube extending into the cavity wherein the drain tube extends proximate to the low point of the cavity.

16. The method according to claim 15, wherein the pH-sensitive membrane is spherical in shape.

17. A method for replacing internal reference solution in a pH glass electrode without having to remove the pH glass electrode from measuring point position, said method comprising:

providing a pH glass electrode, draining used internal reference solution from a cavity via a drain tube and, feeding fresh internal reference solution to the cavity via a feed tube, wherein the pH glass electrode has a sealed glass tube sealed at an end with a pH-sensitive glass membrane, means defining the cavity within the tube, the cavity having a low point towards the end of the tube sealed with the pH-sensitive membrane, and, the internal reference solution in the internal cavity, and, an internal reference electrode extending into the solution, said pH glass electrode characterized by the feed tube and the drain tube extending into the cavity wherein the drain tube extends proximate to the low point of the cavity.

18. The method according to claim 17, wherein the pH-sensitive membrane is spherical in shape.

* * * * *